United States Patent [19]

Maahs et al.

[11] 4,272,633

[45] Jun. 9, 1981

[54] PROCESS FOR THE MANUFACTURE OF TETRACHLOROCYCLOBUTENONE FROM HEXACHLOROCYCLOBUTENE

[75] Inventors: Günther Maahs; Konrad Rombusch, both of Marl, Fed. Rep. of Germany

[73] Assignee: Chemische Werke Huls Aktiengesellschaft, Marl, Fed. Rep. of Germany

[21] Appl. No.: 19,205

[22] Filed: Mar. 9, 1979

[30] Foreign Application Priority Data

Mar. 10, 1978 [DE] Fed. Rep. of Germany ....... 2810398

[51] Int. Cl.³ ..................... C07C 45/27; C07C 49/593
[52] U.S. Cl. .................................... 568/364; 568/381
[58] Field of Search ........................ 260/586 P, 586 R; 568/364, 381

[56] References Cited

U.S. PATENT DOCUMENTS

4,097,530  6/1978  Schroeder et al. ............... 260/586 P

OTHER PUBLICATIONS

Maahs, G. et al., "Synthesen und Derivate der Quadratsaure" Angew. Chem. vol. 78, No. 20. (1966) pp. 927–931.

Hackh's Chemical Dictionary, 2nd Ed. (1938) pp. 905 and 653.

Ann. Chem. (Justus Liebigs) 686 (1965) at pp. 60 and 63.

*Primary Examiner*—Natalie Trousof
*Assistant Examiner*—L. Hendriksen
*Attorney, Agent, or Firm*—Millen & White

[57] ABSTRACT

A process for preparing tetrachlorocyclobutenone from hexachlorocyclobutene comprises reacting (a) hexachlorocyclobutene with I. (b) anhydrous sulphuric acid and (c) sulphur trioxide; or II. (b) anhydrous sulphuric acid and (d) phosphorus pentoxide at a temperature of 30°–140° C.;

the starting materials being present in the following molar ratios at the start of the reaction:

for I,
(a):(c)=0.67–10, and
(b):(c)=0.1–10;

and for II,
(a):(d)=0.67–10 and
(b):(d)=0.5–20.

10 Claims, No Drawings

PROCESS FOR THE MANUFACTURE OF TETRACHLOROCYCLOBUTENONE FROM HEXACHLOROCYCLOBUTENE

BACKGROUND OF THE INVENTION

It is known to manufacture tetrachlorocyclobutenone (perchlorocyclobutenone) by heating 1-alkoxy-pentachloro-1,3-butadiene in the presence of catalysts. The disadvantage of this procedure is that the starting material is not readily accessible.

SUMMARY OF THE INVENTION

Accordingly, it is an object of the present invention to provide a new, simple route for the manufacture of tetrachlorocyclobutenone which uses an inexpensive, readily accessible material as the starting material.

Upon further study of the specification and appended claims, further objects and advantages of this invention will become apparent to those skilled in the art.

These objects have been achieved by providing a process for preparing tetrachlorocyclobutenone from hexachlorocyclobutene which comprises reacting (a) hexachlorocyclobutene with I. (b) anhydrous sulphuric acid and (c) sulphur trioxide; or II. (b) anhydrous sulphuric acid and (d) phosphorus pentoxide at a temperature of 30°–140° C.;
the starting materials being present in the following molar ratios at the start of the reaction:
for I,
(a): (c)=0.67–10, and
(b): (c)=0.1–10;
and for II,
(a): (d)=0.67–10 and
(b): (d)=0.5–20.

DETAILED DISCUSSION

Preferred ranges for the molar ratios of the starting materials are:
for I,
(a): (c)=0.75–5, and
(b): (c)=0.5–5;
and for II,
(a): (d)=0.8–8 and
(b): (d)=0.8–10.

The following molar ratios are particularly preferred:
for I,
(a): (c)=0.83–1.2, and
(b): (c)=0.8–1.2;
and for II,
(a): (d)=1–2 and
(b): (d)=2–5.

The following molar ratios are very particularly preferred:
for I,
(a): (c)=0.9–1.1, and
(b): (c)=0.9–1.1;
and for II,
(a): (d)=1.2–1.8 and
(b): (d)=3–4.

The molar ratios of (b) sulphuric acid: (c) sulphur trioxide can be adjusted to the values mentioned above, for example, by mixing pre-selected amounts of fuming sulphuric acids each containing different amounts of sulphur trioxide; or by mixing concentrated sulphuric acid with fuming sulphuric acid or sulphur trioxide.

When phorphorous pentoxide is used (process variant II), very often technical-grade sulfuric acid is employed. This, of course, contains free water. Since the process of this invention requires that anhydrous sulfuric acid be employed, this free water must be bound up. This can be accomplished by adding the amount of $SO_3$ necessary to bind all the water. Alternatively, an additional amount of $P_2O_5$ can be employed to bind up the water. (Of course, any free water in the sulfuric acid can be similarly bound-up in the reaction variant I.) Of course, the above-defined ratios of b:d are to be satisfied based on the total amount of anhydrous sulfuric acid finally produced.

The process of this invention is carried out at temperatures of 30°–140° C. The preferred temperature ranges for process variant I are 60°–100° C. and especially 70°–90° C. For process variant II, the corresponding ranges are 80°–120° C. and 90°–110° C.

The order of addition of the reactants is not critical but it is highly preferred that the anhydrous sulfuric acid and $SO_3$ or $P_2O_5$ be added to the hexachlorocyclobutene, e.g., poured onto it, with stirring. Typically, reaction times are 0.5–7 hours. General selectivities and conversions for the reaction are 60–95% and 60–95%, respectively. Atmospheric pressure is normally employed.

The starting material hexachlorocyclobutene can be obtained in the pure form (German Patent Application No. P 2,618,557) from the hexachloro-1,3-butadiene which is obtained as a by-product from the technical production of perchlorinated hydrocarbons, and also from hexafluorocyclobutene or 1,2-dichlorotetrafluorocyclobutene [J. Org. Chem. 31, 1,551 (1966) and Tetrahedron Letters 16, 1,061 (1971)]. Hexachloro-1,3-butadiene fractions rich in hexachlorocyclobutene [Agnew. Chem. 78, 927 (1966)] can also be employed in the process of this invention. The hexachloro-1,3-butadiene present as an impurity in such mixtures of hexachlorocyclobutene (e.g., 50–70% of the mixture) virtually does not participate in the reaction and also does not form any by-products. Thus, after the reaction, it can be separated from the other reaction products in a simple manner, by distillation. Hexachloro-1,3-butadiene thus acts as an inert diluent.

Tetrachlorocyclobutenone can be used as a bactericide or an an intermediate product, for example, for the manufacture of quadratic acid or esters thereof. It is also a starting material for the manufacture of other derivatives containing a four-membered ring and of linear, highly chlorinated compounds [Liebigs Ann. Chem. 686, 55 (1965)]. See, for example, copending U.S. Application Ser. No. 19,204 to Maahs et al which was filed concurrently with this application, whose disclosure is incorporated by reference herein for the use of tetrachlorocyclobutenone to prepare 2,3,4,4,tetrachloro-3-butenoic acid esters.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In a 1 liter flask, 341 g of 39.8% strength fuming sulphuric acid (oleum) were poured onto 500 g of 97.5% pure hexachlorocyclobutene [487.5 g (1.87 moles) of hexachlorocyclobutene; remainder hexachloro-1,3-butadiene], with stirring (molar ratio of hexachlorcyclobutene:sulphuric acid:sulphur trioxide=1:1.1:0.9). The mixture was heated at 80° C. for 5 hours. After cooling, the reaction product was poured slowly into a mixture of ice and sodium chloride, with vigorous stirring, and the organic phase was then separated immediately from the aqueous phase. A mixture of 326 g of tetrachlorocyclobutenone, 25 g of hexachlorocyclobutene and 23 g of hexachloro-1,3-butadiene was obtained. The selectivity of the reaction was thus 90.5% of theory with a conversion of 92% of theory.

EXAMPLE 2

In a 1 liter flask, 200.6 g of 50% strength fuming sulphuric acid (oleum) were poured onto 300 g of 97.5% pure hexachlorocyclobutene [292.5 g (1.12 moles) of hexachlorocyclobutene; remainder hexachloro-1,3-butadiene], with stirring (molar ratio of hexachlorocyclobutene:sulphuric acid:sulphur trioxide=1:0.9:1.1). The mixture was heated at 80° C. for 5 hours. After cooling, the reaction product was poured slowly into a mixture of ice and sodium chloride, with vigorous stirring. The organic phase was then separated immediately from the aqueous phase. A mixture of 185 g of tetrachlorocyclobutenone, 14.4 g of hexachlorocyclobutene and 7.2 g of hexachloro-1,3-butadiene was obtained. The selectivity of the reaction was thus 88% of theory with a conversion of 95% of theory.

EXAMPLE 3

In a 500 cc flask, 46.8 g of 58.2% strength fuming sulphuric acid were poured onto 100 g of 94.7% pure hexachlorocyclobutene [94.7 g (0.36 mole) of hexachlorocyclobutene; remainder hexachloro-1,3-butadiene], with stirring (molar ratio of hexachlorocyclobutene:sulphuric acid:sulphur trioxide=1:0.53:0.89). The mixture was heated at 100° C. for 3 hours. After cooling, the reaction product was poured slowly onto ice, with vigorous stirring, and the organic phase was separated immediately from the aqueous phase. The latter was extracted twice with petroleum ether. After drying with a little sodium sulphate, a fractional distillation was carried out. The main fractions consisted of 43.1 g of tetrachlorocyclobutenone, 33.2 g of hexachlorocyclobutene and 5.0 g of hexachloro-1,3-butadiene. The selectivity of the reaction was thus 89% of theory with a conversion of 61% of theory.

EXAMPLE 4

In a 2 liter flask, 682 g of 39.8% strength fuming sulphuric acid were poured onto 1,000 g of 97.5% pure hexachlorocyclobutene [975 g (3.74 moles) of hexachlorocyclobutene; remainder hexachloro-1,3-butadiene], with stirring (molar ratio of hexachlorocyclobutene:sulphuric acid:sulphur trioxide=1:1.1:0.9). The mixture was heated at 70° C. for 7 hours. After cooling, the reaction product was poured slowly onto ice, with vigorous stirring, and the organic phase was separated immediately from the aqueous phase. The latter was extracted twice with petroleum ether. After drying with a little sodium sulphate, the petroleum ether was distilled off. The residue consisted of 603 g of tetrachlorocyclobutenone, 43 g of hexachlorocyclobutene and 25 g of hexachloro-1,3-butadiene. The selectivity of the reaction was thus 86% of theory with a conversion of 93% of theory.

EXAMPLE 5

In a 500 cc flask, 68.3 g of 45% strength fuming sulphuric acid were poured onto a mixture of 97.5 g of hexachlorocyclobutene (0.374 mole) and 102.5 g of hexachloro-1,3-butadiene, with stirring (molar ratio of hexachlorocyclobutene:sulphuric acid:sulphur trioxide=1:1:1). The mixture was heated at 80° C. for 1 hour. After cooling, the reaction product was poured slowly onto a mixture of ice and sodium chloride, with vigorous stirring, and the organic phase was separated immediately from the aqueous phase. It consisted of 67.5 g of tetrachlorocyclobutenone, 5.5 g of hexachlorocyclobutene and 101.4 g of hexachloro-1,3-butadiene. The selectivity of the reaction was thus 92% of theory with a conversion of 94% of theory.

EXAMPLE 6

In a 500 cc flask, 68.3 g of 45% strength fuming sulphuric acid were poured onto a mixture of 100 g of hexachlorocyclobutene (0.383 mole) and 233 g of hexachloro-1,3-butadiene, with stirring (molar ratio of hexachlorocyclobutene:sulphuric acid:sulphur trioxide=1:1:1). The mixture was heated at 80° C. for 1 hour. After cooling, the reaction product was poured slowly onto a mixture of ice and sodium chloride, with vigorous stirring, and the organic phase was separated immediately from the aqueous phase. It consisted of 66.3 g of tetrachlorocyclobutenone, 6.7 g of hexachlorocyclobutene and 231.6 g of hexachloro-1,3-butadiene. The selectivity of the reaction was thus 90% of theory with a conversion of 93% of theory.

EXAMPLE 7

In a 2 liter flask, 66.4 g of 58.5% strength fuming sulphuric acid were poured onto 103.7 g of 96.4% pure hexachlorocyclobutene [100 g (0.383 mole) of hexachlorocyclobutene; remainder hexachloro-1,3-butadiene], with stirring (molar ratio of hexachlorocyclobutene:sulphuric acid:sulphur trioxide=1:0.73:1.27). The mixture was heated at 80° C. for 1 hour. After cooling, the reaction product was poured slowly onto ice, with vigorous stirring, and the organic phase was separated immediately from the aqueous phase. The latter was extracted twice with petroleum ether. After drying with a little sodium sulphate, the petroleum ether was distilled off. The residue consisted of 55.2 g of tetrachlorocyclobutenone, 7.7 g of hexachlorocyclobutene and 2.6 g of hexachloro-1,3-butadiene. The selectivity of the reaction was thus 74% of theory with a conversion of 93% of theory.

EXAMPLE 8

In a 500 cc flask, 105.7 g of 29% strength fuming sulphuric acid were poured onto 102.5 g of 97.6% pure hexachlorocyclobutene [100 g (0.383 mole) of hexachlorocyclobutene; remainder hexachloro-1,3-butadiene], with stirring (molar ratio of hexachlorocyclobutene:sulphuric acid:sulphur trioxide=1:2:1). The mixture was heated at 80° C. for 1 hour. After cooling, the reaction product was poured slowly into a mixture of ice and sodium chloride, with vigorous stirring, and the organic phase was then separated immediately from the aqueous phase. A mixture of 41.1 g of tetrachlorocyclobutenone, 9.5 g of hexachlorocyclobutene and 2.4 g of hexachloro-1,3-butadiene was obtained. The selectivity of the reaction was thus 72% of theory with a conversion of 91% of theory.

EXAMPLE 9

In a 500 cc flask, 143.4 g of 21.4% strength fuming sulphuric acid (oleum) were poured onto 209.8 of 95.3% pure hexachlorocyclobutene [199.9 g (0.766 mole) of hexachlorocyclobutene; remainder hexachloro-1,3-butadiene], with stirring (molar ratio of hexachlorocyclobutene:sulphuric acid:sulphur trioxide=1:1.5:0.5). The mixture was heated at 80° C. for 5 hours. After cooling, the reaction product was poured slowly into a mixture of ice and sodium chloride, with vigorous stirring, and the organic phase was then separated immediately from the aqueous phase. A mixture of 83.2 g of tetrachlorocyclobutenone, 58.9 g of hexachlorocyclobutene and 8.6 g of hexachloro-1,3-butadiene was obtained. The selectivity of the reaction was thus 75% of theory with a conversion of 71% of theory.

EXAMPLE 10

In a 500 cc flask, a mixture of 75.1 g of 100% strength sulphuric acid and 27.2 g of phosphorus pentoxide was added to a mixture of 99.9 g of hexachlorocyclobutene (0.383 mole) and 2.6 g of hexachloro-1,3-butadiene, with stirring (molar ratio of hexachlorocyclobutene:sulphuric acid:phosphorus pentoxide=1:2:0.5). The mixture was heated at 100° C. for 3 hours. After cooling, the reaction product was poured slowly onto a mixture of ice and sodium chloride, with vigorous stirring, and the organic phase was separated immediately from the aqueous phase. It consisted of 51.8 g of hexachlorocyclobutenone, 9.7 g of hexachlorocyclobutene and 4.0 g of hexachloro-1,3-butadiene. The selectivity of the reaction was thus 89% of theory with a conversion of 74% of theory.

EXAMPLE 11

In a 1 liter flask, a mixture of 78 g of concentrated sulphuric acid and 78.5 g of phosphorus pentoxide was poured onto 100 g of 96% pure hexachlorocyclobutene [96 g (0.368 mole) of hexachlorocyclobutene; remainder hexachloro-1,3-butadiene], with stirring (molar ratio of hexachlorocyclobutene:sulphuric acid:phosphorus pentoxide=1:2:1). The mixture was heated at 100° C. for 3 hours. After cooling, the reaction mixture was poured onto ice, the organic phase was then separated immediately from the aqueous phase and the latter was extracted three times with petroleum ether. The petroleum ether solution and the organic phase were combined and dried with sodium sulphate, the petroleum ether was distilled under normal pressure and the residue was subjected to fractional distillation under 35 mbars. 43.6 g of tetrachlorocyclobutenone, 14.3 g of hexachlorocyclobutene and 3.6 g of hexachloro-1,3-butadiene were obtained. The selectivity of the reaction was 69.0% of theory with a conversion of 85% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing tetrachlorocyclobutenone from hexachlorocyclobutene, which comprises reacting
(a) hexachlorocyclobutene with
I. (b) anhydrous sulphuric acid and (c) sulphur trioxide; or
II. (b) anhydrous sulphuric acid and (d) phosphorus pentoxide
at a temperature of 30°–140° C.;
the starting materials being present in the following molar ratios at the start of the reaction:
for I,
  (a): (c)=0.67–10:1 and
  (b): (c)=0.1–10:1;
and for II,
  (a): (d)=0.67–10:1 and
  (b): (d)=0.5–20:1.

2. The process of claim 1, wherein reaction I is employed and the temperature is 60°–100° C.

3. The process of claim 1, wherein reaction II is employed and the temperature is 80°–120° C.

4. The process of claim 1, wherein the starting material hexachlorocyclobutene contains an inert diluent.

5. The process of claim 4, wherein hexachloro-1,3-butadiene is the inert diluent.

6. The process of claim 1, wherein the molar ratios are
for I,
  (a): (c)=0.75–5:1, and
  (b): (c)=0.5–5:1;
and for II,
  (a): (d)=0.8–8:1 and
  (b): (d)=0.8–10:1.

7. The process of claim 1, wherein the molar ratios are
for I,
  (a): (c)=0.83–1.2:1, and
  (b): (c)=0.8–1.2:1;
and for II,
  (a): (d)=1–2:1 and
  (b): (d)=2–5:1.

8. The process of claim 1, wherein the molar ratios are
for I,
  (a): (c)=0.9–1.1:1, and
  (b): (c)=0.9–1.1:1;
and for II,
  (a): (d)=1.2–1.8:1 and
  (b): (d)=3–4:1.

9. The process of claim 1, wherein reaction I is employed.

10. The process of claim 1, wherein reaction II is employed.

* * * * *